United States Patent [19]
Amundsen et al.

[11] Patent Number: 4,839,386

[45] Date of Patent: Jun. 13, 1989

[54] IONIC BIS (DICARBOXYLATO) PALLADATE (II)

[75] Inventors: Alan R. Amundsen, Somerville; Eric W. Stern, Mountainside, both of N.J.

[73] Assignee: Engelhard Corporation, Menlo Park, N.J.

[21] Appl. No.: 85,283

[22] Filed: Aug. 12, 1987

Related U.S. Application Data

[60] Continuation of Ser. No. 798,202, Nov. 14, 1985, abandoned, Division of Ser. No. 642,235, Aug. 17, 1984, Pat. No. 4,578,490, Continuation of Ser. No. 392,817, Jun. 28, 1982, abandoned.

[51] Int. Cl.$^4$ .............................................. A61K 31/28

[52] U.S. Cl. ................................................... 514/492
[58] Field of Search ....................................... 514/492

[56] References Cited

PUBLICATIONS

Schmelz et al., J.A.C.S. vol. 81, pp. 287–290 (1959).

*Primary Examiner*—Jerome D. Goldberg

[57] ABSTRACT

There are described ionic bis(dicarboxylato)palladate(II) products derived from aliphatic and aromatic dicarboxylic acids useful in the treatment of malignant animal tumors sensitive thereto. Certain of the compounds are novel.

21 Claims, No Drawings

IONIC BIS (DICARBOXYLATO) PALLADATE (II)

This is a division of application Ser. No. 06/642,235 filed Aug. 17, 1984 now U.S. Pat. No. 4,578,490 which is a continuation of Ser. No. 06/392,817 filed Jun. 28, 1982 now abandoned. This is a continuation of co-pending application Ser. No. 06/798,202 filed on Nov. 14, 1985 now abandoned.

This invention relates to a class of ionic bis(dicarboxylato)palladate(II) compounds certain of which are novel, pharmaceutical compositions comprising same and a method for the treatment of malignant tumor cells which are sensitive to said compounds via the administration of said compositions.

There are very few palladium complexes which are useful in the treatment of malignant animal tumor cells and it is an object of this invention to add to the known family of anti-tumor agents by providing a new class of ionic palladium compounds.

BACKGROUND

The discovery that platinum complexes are active against tumors has brought about a renewed interest in metal complexes as a source for anti-cancer agents. Cisplatin, cis-$[Pt(NH_3)_2-Cl_2]$, for example, has been singularly successful in bringing about a regression of testicular and ovarian tumors and, as a result, other platinum derivatives have been investigated for anti-tumor activity.

These developments have led to the exploitation of structure-activity relationships including the synthesis of palladium analogs. Most of these efforts have been directed to the preparation of neutral palladium compounds. However, many of these have failed to show any discernible activity and, as a rule, have low solubility in aqueous solutions. Moreover, structure-activity relationships which have been developed for platinum compounds would predict that only neutral compounds would have anti-tumor activity. (M. J. Cleare and J. D. Hoeschele; "Bioinorganic Chemistry", Vol. 2: page 187 (1973); and M. J. Cleare; "Coordination Chemistry Reviews", Vol. 12: page 349 (1974).

THE INVENTION

This invention relates to the use of a class of ionic palladium compounds which are soluble in aqueous solution and which are useful in the treatment of malignant animal tumors sensitive thereto. These compounds exhibit excellent activity against malignant tumor cells sensitive thereto in animals as well as low mammalian toxicity.

More specifically, this invention relates to the use of alkali metal and alkaline earth metal bis(dicarboxylato)-palladate(II) compounds derived from aliphatic and aromatic dicarboxylic acids. The palladium in said compounds is shared between two rings which contain from 6-7 atoms per ring.

The compounds used in this invention possess the following structural formula:

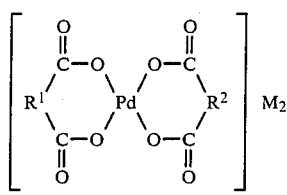
(I)

wherein $R^1$ and $R^2$ are the same or different and represent the following: methylene or ethylene; cycloalkylene of the formula:

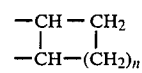

wherein n is an integer having a value of 2-3; alkylidene of 2-4 carbon atoms; cycloalylidene containing from 4-6 nuclear carbon atoms; o-phenylene of the formula:

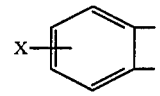

wherein X is selected from the group consisting of hydrogen, halogen and $C_{1-6}$ alkyl; aralkylidene of the formula:

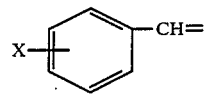

substituted methylidene of the formula: $=CR^3R^4$ wherein $R^3$ and $R^4$ are selected from the group consisting of hydrogen, halogen and hydroxy; or keto;

M is an alkali metal or $M_2$ is an alkaline earth metal. Compounds wherein $R^1$ and $R^2$ are both methylene are known from Gmelin's Hambuch Der Anorganischem Chemie, Vol. 65: page 320 (1987); as well as J.A.C.S., Vol. 81: page 287 (1959); J. Organic Chemistry, Vol. 41: page 2049 (1976) and others. The other compounds are believed novel.

The following compounds are useful in the treatment of malignant tumor cell sensitive thereto chemotherapy over a wide range of dosages and they constitute a preferred subgroup of pharmacologically active products within the scope of this invention:

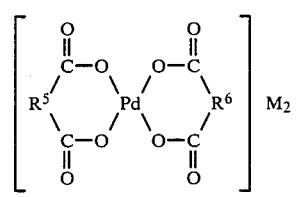
(Ia)

wherein $R^5$ and $R^6$ are identical moieties selected from among: alkylidene of 2-4 carbon atoms; cycloalkylidene containing from 4-6 nuclear carbon atoms; o-phenylene of the formula:

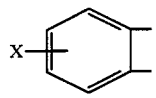

wherein X is selected from the group consisting of hydrogen, halogen and $C_{1-6}$ alkyl: hydroxymethylidene; and keto; and M is an alkali metal.

The aforedescribed products (Ia) exhibit good solubility in aqueous solutions and the dosage levels required for anti-tumor activity against malignant animal tumor cells sensitive thereto is not narrowly critical.

PREPARATIVE METHODS

The products useful in this invention may be prepared by treating an alkali metal or alkaline earth metal carboxylate with a palladium salt. Suitable salts include the palladium halides such as palladium chloride or a functionally equivalent salt having leaving groups similar to halide as, for example, palladium nitrate or a palladium carboxylate such as palladium acetate. Tetrahalopalladates or equivalent salts containing other leaving groups are also suitable. Said palladium salt is added to a concentrated solution of the alkali metal or alkaline earth metal form of the dicarboxylate starting material ($R^1(COOM)_2$,infra) and the mixture is warmed gently or maintained at room temperature over an extended period with stirring. The resulting precipitate is then filtered and washed with a suitable solvent such as ethanol to afford the desired product (I). These products may contain acid residues which are the same or different. The following equation illustrates the preparation of products having identical acid functions or residues but products having a mixed acid. functionally may also be obtained by treating said palladium salt with two distinct acids either in the form of a mixture or individually in steps:

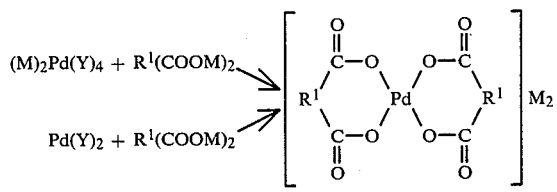

wherein M is an alkali metal or $M_2$ is an alkaline earth metal; Y is a leaving group such as halo, for example, chloro, bromo and the like, nitrato ($NO_3^-$) or alkylcarboxy such as acetoxy and the like; and the two $R^1$ radicals are identical moieties as defined hereinabove.

The dicarboxylate starting materials in the foregoing process are obtained via neutralization of the corresponding dicarboxylic acid precursor with alkali metal hydroxide or an alkaline earth metal hydroxide. If desired, the resulting solution may be evaporated to dryness and the residue recrystallized from water to afford an essentially pure alkali metal or alkaline earth metal dicarboxylate which may be used directly in the aforedescribed process.

The products of this invention may also be obtained via the reaction of palladium hydroxide with a dicarboxylic acid salt [$R^1(COOM)_2$]. This procedure is illustrated by the following equation in which $R^1(COOM)_2$ is treated with $Pd(OH)_2$ to afford a bis(discarboxylato)-palladate(II) having identical acid (i.e., $R^1$) residues:

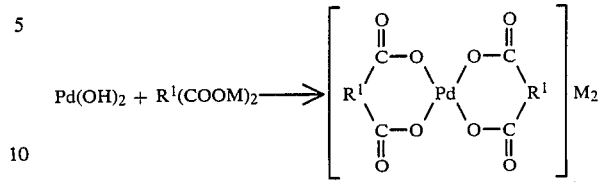

wherein M is as defined above and $R^1$ represents the residue of a dicarboxylic acid as hereinbefore defined. In this instance the acid residues are derived from a single dicarboxylic acid and they are identical. Those products in which the acid functions are dissimilar can be prepared in an essentially identical manner by treating the $Pd(OH)_2$ first with one form of dicarboxylate salt ($R^2COOM$) at half the stoichiometric concentration and then with another ($R^2COOM$) in an identical amount. Temperature is not critical to the aforedescribed process and ambient temperatures may be employed; however, it is desirable in some instances to facilitate the process by the application of heat and the use of agitation means. The products are obtained from solution in the form of precipitates which may be isolated by filtration and then washed and dried. Recrystallization from alcohol affords an essentially pure product.

PHARMACOLOGY

These products are useful in the treatment of malignant tumor cells sensitive thereto in animals, as, for example, Sarcoma 180 ascites in mammals such as mice. This cell effect also may extend to other sarcomas and to such other tumor cells as the following: lymphoid leukemia, lymphosarcoma, myelocytic leukemia, malignant lymphoma, squamous cell carcinoma, adenocarcinoma, scirrhous carcinoma, malignant melanoma, seminoma, teratoma; choriocarcinoma, embryonalcarcinoma, cystadenocarcinoma, endometroidcarcinoma or neuroblastoma and the like. In addition, said complexes may be useful as anti-viral, anti-inflammatory, anti-bacterial and anti-parasitic agents.

They may be administered parenterally or orally in admixture with a non-toxic pharmacologically acceptable inert carrier or diluent in any of the usual pharmaceutical forms. These include solid and liquid oral unit dosage forms such as tablets, capsules, powders and suspensions or solutions and suspensions for subcutaneous, intramuscular, intravenous or intra-arterial injection.

The term "unit dosage" refers to physically discrete units which may be administered in single or multiple dosages each containing a predetermined quantity of the active ingredient in association with the required diluent, carrier or vehicle. The quantity of active ingredient is the amount of the complex which is needed to produce the desired therapeutic effect.

A typical unit dosage consists essentially of from about 10–500 mg. of active ingredient; however, the form in which said ingredient is administered and the frequency of administration is usually determinative of the concentration. Thus, for example, oral unit dosage forms containing 10–500 mg. of active ingredient may be administered one or more times per day depending upon the severity of the tumor which is sought to be treated and the condition of the host animal containing the tumor cells sensitive to the active ingredient. By contrast, parenteral administration generally requires from about 20-250 mg. of the active ingredient per unit dosage administered as a daily dose or as a fraction thereof depending upon whether the regimen calls for administration once, twice, three or four times daily.

By contrast to the "unit dosage", the effective dose is that dosage which is needed to achieve the desired anti-tumor cell effect against tumor cells sensitive thereto. In general, this dosage lies within the range of from about 6-1200 mg. of the active ingredient per kg. of body weight of the host animal. A preferred concentration lies within the range of from about 10-500 mg./kg. of body weight. For oral administration it has been found that an effective dose of 30-1200 mg./kg. is most suitable, whereas, in the case of parenteral administration it is usually advisable to employ from about 6-200 mg./kg. These dosages are well below the toxic or lethal dose and they may be varied over a wide range.

In this invention the term "pharmacologically acceptable inert carrier or diluent" denotes a non-toxic substance which, when mixed with the active ingredient, renders it more suitable for administration. Compositions intended for oral administration may include such carriers or diluents as corn starch, potato starch, sodium carboxymethyl cellulose, ethyl cellulose, cellulose acetate, powdered gum tragacanth, gelatin, alginic acid, agar, stearic acid or the sodium, calcium and magnesium salts or stearic acid, sodium lauryl sulfate, polyvinylpyrrolidone, sodium citrate, calcium carbonate and dicalcium phosphate. Said compositions may also contain non-toxic adjuvants and modifiers such as dyes, buffering agents, preservatives, surfactants, emulsifiers, flavoring agents or biocides and the like.

Tablets are prepared by mixing a complex of this invention in a suitably comminuted or powdered form with a diluent or base such as starch, kaolin, di-calcium phosphate and the like. The resulting mixture can be granulated by wetting with a binder such as a syrup, starch (paste), acacia mucilage or solutions of cellulosic or polymeric materials, whereafter, the wetted mixture is forced through a screen. As an alternative to granulating, the powdered mixture can be run through a tablet machine and imperfectly formed slugs broken into granules. The granules are lubricated to prevent sticking to the tablet-forming dies via the addition of stearic acid, a stearate salt, talc or mineral oil and the lubricated mixture is then compressed into tablets. The complexes can also be combined with free flowing inert carriers followed by compression into tablets without going through the granulating or slugging steps. A protective coating or sealing coat of shellac, sugar or polymeric material and a polished coating of wax can also be provided. Dyestuffs may be added to distinguish different unit dosages.

Capsules are formulated by preparing a powdered mixture, according to the procedure hereinbefore described and pouring said mixture into preformed gelatin sheaths. A lubricant such as talc, magnesium stearate or calcium stearate can be added as an adjuvant prior to the filling operation. A glidant such as colloidal silica may be added to improve the flow characteristics and a disintegrating or solubilizing agent may also be added to enhance the effectiveness of the medicament upon ingestion.

Powders are prepared by comminuting the compound to a fine size and mixing with a similarly comminuted pharmaceutical diluent or carrier such as an edible carbohydrate as, for example, starch. Sweetening agents and flavorings, preservatives and dispersing and/or coloring agents may also be employed.

Oral fluids such as syrups and elixirs are prepared in unit dosage form so that a given quantity of medicament, such as a teaspoonful, will contain a predetermined amount of the active ingredient. Suspensions can be formulated by dispersing the active ingredient in a non-toxic vehicle in which it is essentially insoluble.

Fluid unit dosage forms for parenteral administration can be prepared by placing a measured amount of the complex in an ampoule or vial which is sterilized and sealed. An accompanying vial or vehicle can be provided for mixing with said complex prior to administration.

This invention also provides for combining two or more of the subject complexes into a single unit dosage form or, alternatively, combining one or more of said complexes with other known anti-tumor agents, therapeutic agents or nutritive agents and the like so as to enhance or complement the anti-tumor effect.

The preferred compositions for oral administration are tablets in which the lactate complex is present in quantities of 10-500 mg. but, preferably, 50-300 mg. in a pharmaceutically acceptable orally ingestible solid carrier. If desired, the composition may also contain flavors, binders, lubricants and other excipients known in the art.

A preferred alternative or oral administration is the soft gelatin capsule. Such a composition may contain from 10-500 mg. but, preferably, 50-300 mg. by weight of active ingredient dissolved or suspended in vegetable oil, peanut oil, alcohol or glycerine and the like.

The following embodiments illustrate representative unit dosage forms:

Compressed Tablets

A tablet suitable for swallowing is prepared by mixing the following ingredients:

| | |
|---|---|
| Potassium Bis(ethylmalonato)palladate(II) | 150 mg. |
| Niacinamide | 50 mg. |
| Calcium Pantothenate | 20 mg. |
| Magnesium Sulfate | 50 mg. |
| Zinc Sulfate | 50 mg. |
| Magnesium Stearate | 10 mg. |
| | 330 mg. |

The potassium bis(ethylmalonato)palladate(II), niacinamide, calcium pantothenate, magnesium sulfate, zinc sulfate and magnesium stearate (5.0 mg.) are mixed and compressed into slugs. The slugs are then broken into granules and sifted through an 8 mesh screen. Additional magnesium stearate (5.0 mg.) is added and the mixture is then compressed into tablets suitable for oral administration.

Soft Gelatin Capsule

A soft elastic gelatin capsule is filled with the following ingredients:

| | |
|---|---|
| Potassium Bis(Phthalato)palladate(II) | 200 mg. |
| Wheat germ oil | 50 mg. |

| | |
|---|---|
| Sunflower seed oil | 100 mg. |
| | 350 mg. |

The potassium bis(phthalato)palladate(II) and wheat germ oil are mixed with sunflower seed oil and the resulting mixture is poured into gelatin capsules suitable for oral administration. An alternative embodiment provides for substituting sunflower seed oil and wheat germ oil with equal amounts of peanut oil to obtain an otherwise similar capsule which is also suitable for oral administration

Dry Filled Capsule

A hard dry-filled capsule may be prepared from the following ingredients:

| | |
|---|---|
| Potassium Bis(Ketomalonato)palladate(II) | 150 mg. |
| Niacinamide | 50 mg. |
| Calcium Pantothenate | 10 mg. |
| | 210 mg. |

The potassium bis(ketomalonato)palladate(II) is reduced to a No. 60 powder. Niacinamide and calcium pantothenate are passed through a No. 60 bolting cloth and these ingredients are added to the potassium bis(ketomalonato)palladate(II). This combination of ingredients is mixed for 10 minutes and then poured into a No. 3 size gelatin capsule.

Dry Powder

The following composition illustrates a representative dosage in dry powder form. In this embodiment the active ingredient is water soluble and it is combined with up to 60% by weight of a suitable flavoring agent. All quantities are in a weight-percent relationship.

| | |
|---|---|
| Potassium Bis(Phthalato)palladate(II) | 25–90% |
| Flavoring Agent | 10–60% |
| Preservative | 0–1.0% |

The potassium bis(phthalato)palladate (II) flavoring agent and preservative are thoroughly blended to afford a homogeneous dry powder which is readily soluble in water. The resulting formulation may be blended with other therapeutic agents to afford combination-type medicinals. Alternatively, said powder may be dissolved in a pharmacologically acceptable diluent to afford a solution which is suitable for oral administration.

Compositions intended for parenteral administration may include such diluents and carriers as water-miscible solvents as, for example, sesame oil, groundnut oil, and aqueous propylene glycol. Typical of said compositions are solutions which contain the active ingredient in sterile form. An embodiment illustrating a dosage form suitable for intravenous injection is set forth below.

Parenteral Solution

Injectable solutions can be formulated by mixing an ampoule of active ingredient with an ampoule of sterile diluent:

| | |
|---|---|
| Ampoule: Potassium Bis(Cyclobutanedi-carboxylato)palladate(II) | 150 mg. |
| Ampoule: Sterile Water (Diluent for Injection) | 2 cc. |

The potassium bis(cyclobutanedicarboxylato)palladate(II) and water are mixed thoroughly immediately prior to administration. If desired, one or more other active ingredients may be added to provide an injectable solution having enhanced therapeutic activity.

The following embodiments illustrate the methods by which the products (I) of this invention are obtained; however, it is to be understood that said embodiments are merely illustrative and they are not to be construed as being limitative of the invention herein described and claimed.

PREFERRED EMBODIMENTS

EXAMPLE 1

Potassium Bis(Ethylmalonato)palladate(II)

Ethylmalonic acid (1.58, 15 mmoles) and potassium hydroxide (1.68g, 30 mmoles) were dissolved in water (15 ml) and solid palladium chloride (1.065 g, 6 mmoles) was added. The mixture was stirred for 30 minutes and the resulting solution was added to ethanol (100 ml) and placed in a freezer for 2.5 hours. The product was filtered, washed with two 15 ml portions of ethanol and vacuum dried to afford 1.48 g, (55.5%) yield of potassium bis(ethylmalonato)palladate(II). This product was soluble in water in an amount of 70 mg/ml at room temperature. Palladium analysis for $K_2PdC_{10}H_{12}O_8 \cdot H_2O$: Calculated: 22.99% Found: 22.245

EXAMPLE 2

Potassium Bis(Ketomalonato)palladate(II)

Ketomalonic acid (0.68 g, 5 mmoles) was dissolved in 1M potassium hydroxide (10 ml, 10 mmoles) and palladium chloride (0.355 g, 2 mmoles) was added. The mixture was stirred for 1.5 hours and the resulting solution was cooled to 0° C. A yellow precipitate formed. An equal volume of ethanol was added and the precipitate was filtered, washed with three of 10 ml portions of ethanol and vacuum dried. There was thus obtained 0.7 g (68.1%) of potassium bis(ketomalonato)palladate(II). This product was soluble in water in an amount of 6.7 mg/ml at room temperature. Palladium analysis for $K_2PdC_6O_{10} \cdot 5H_2O$: Calculated: 20.00% Found: 20.71%

EXAMPLE 3

Potassium Bis(Methylmalonato)palladate(II)

Methylmalonic acid (0.59 g, 5 mmoles) was dissolved in 1M potassium hydroxide (10 ml, 10 mmoles) and palladium chloride (0.355 g, 2mmoles) was added. The mixture was stirred at room temperature for 45 minutes during which time the palladium chloride dissolved and a yellow precipitate formed. This precipitate was filtered washed with 10 ml of water and two 10 ml portions of ethanol and then vacuum dried. The yield of potassium bis(methylmalonato)palladate(II) was 0.42 g (50.4%). This product was soluble in water in an amount of 21 mg/ml at room temperature. Palladium analysis for $K_2PdC_8H_8O_8 \cdot 2H_2O$: Calculated 23.50% Found: 23.75%

EXAMPLE 4

Potassium Bis(Tartronato)palladate(II)

Tartronic acid (0.60 g, 5 mmoles) was dissolved in 1M potassium hydroxide (10 ml, 10 mmoles) and solid palladium chloride (0.355 g, 2 mmoles) was added. The mixture was stirred at room temperature for one hour during which time a yellow precipitate formed. This precipitate was filtered, washed with water (10 ml) and two 10 ml portions of ethanol and vacuum dried. The yield of potassium bis(tartronato)palladate(II) was 0.75 g (98.3%). This product was soluble in water in an amount of 2 mg/ml at room temperature. Palladium analysis for $K_2PdC_6H_4O_{10}\cdot 2H_2O$: Calculated: 25.05% Found: 24.67%.

EXAMPLE 5

Potassium Bis(phthalato)palladate(II)

Phthalic acid (0.83 g, 5 mmoles) was dissolved in 1M potassium hydroxide (10 ml, 10 mmoles) and solid palladium chloride (0.355 g, 2 mmoles) was added. This mixture was stirred at room temperature for 1.75 hours and it resulted in the formation of a reddish solution. Acetone (100 ml) was added and the solution was placed in a freezer overnight. A yellow precipitate formed and this material was filtered, washed with three 10 ml portions of acetone and vacuum dried. There was thus obtained 0.86 g (83.9%) of potassium bis(phthalato)palladate(II). This product was soluble in water to the extend of 80 mg/ml at room temperature. Palladium analysis for $K_2PdC_{16}H_8O_8$: Calculated: 20.75% Found: 23.67%.

EXAMPLE 6

Potassium Bis(Cyclobutanedicarboxylato)palladate(II)

1,1-Cyclobutanedicarboxylic acid (1.44 g, 10 mmoles) was suspended in water (15 ml) and potassium hydroxide (1.12 g, 20 mmoles) was added. Upon dissolution of said acid solid palladium chloride (0.7 g, 4 mmoles) was added and the mixture was stirred at room temperature for 2.5 hours. Ethanol (50 ml) was added and the mixture was cooled to 0° C. to afford a yellow precipitate. This precipitate was filtered, washed with two 10 ml portions of ethanol and vacuum dried. The yield of potassium bis(cyclobutanedicarboxylato)palladate(II) was 1.34 g (71.5%). This product was soluble in water in an amount of 200 mg/ml at room temperature. Palladium analysis for $K_2PdC_{12}H_{12}O_8\cdot 3H_2O$: Calculated: 20.34% Found: 20.01%.

EXAMPLE 7

Potasium Bis(Dimethylmalonato)palladate(II)

Dimethylmalonic acid (1.32 g, 10 mmoles) was suspended in water (10 ml) and potassium hydroxide (1.12 g, 20 mmoles) was added. Palladium chloride (0.71 g, 4 mmoles) was added to the resulting solution and the mixture was stirred at room temperature for two hours. Ethanol (50 ml) was added and the mixture was refrigerated for 30 minutes. The resulting tan precipitate was filtered washed with two 10 ml portions of ethanol and vacuum dried. The yield of potassium bis(dimethylmalonato)palladate(II) was 1.55 g (87.2%). This product was soluble in water in an amount of 300 mg/ml at room temperature. Palladium analysis for $K_2PdC_{10}H_{12}O_8\cdot 4H_2O$:
Calculated: 20.50%
Found: 20.73%.

By repeating the procedure of Example 1, using dicarboxylic acids other than ethylmalonic acid, a variety of bis(dicarboxylato)palladate(II) products are obtained. The following equation and accompanying Table illustrate the method of Example 1, the starting materials which may be employed and the products obtained thereby:

TABLE 1

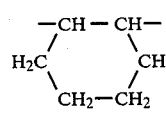

| Example | R$^1$ | M |
|---|---|---|
| 8 | —CH(C$_2$H$_5$)— | Na |
| 9 | —CH(OH)— | Li |
| 10 | —C(CH$_2$)$_3$— | Ca |
| 11 | —C(CH$_2$)$_4$— | K |
| 12 | —C(CH$_2$)$_5$— | K |
| 13 | —CH(C$_6$H$_5$)* | K |
| 14 | —CH[—CH(CH$_3$)$_2$]— | K |
| 15 | —CHCl— | K |
| 16 | —CCl$_2$— | K |
| 17 | —CH$_2$CH$_2$— | K |
| 18 | 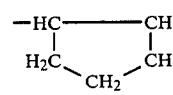 | K |
| 19 | 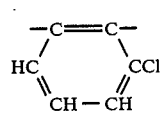 | K |
| 20 |  | K |

*C$_6$H$_5$ represents phenyl.

Those products in which the acid functions are dissimilar may be obtained by adding PdCl$_2$ to a mixture of potassium dicarboxylates. This method, the starting materials employed and the resulting palladates(II) are illustrated by the following equation and accompanying Table:

TABLE 2

$R^1(COOK)_2 + R^2(COOK)_2 + PdCl_2 \longrightarrow$ $$\left[ \begin{array}{c} \text{R}^1\diagup\!\!\!\!\begin{array}{c}\text{C}-\text{O}\\\text{C}-\text{O}\end{array}\!\!\!\!\diagdown\text{Pd}\diagup\!\!\!\!\begin{array}{c}\text{O}-\text{C}\\\text{O}-\text{C}\end{array}\!\!\!\!\diagdown\text{R}^1 \end{array} \right] K_2$$

| Example | R$^1$ | R$^2$ |
|---|---|---|
| 21 | —CH$_2$— | —CH(C$_2$H$_5$)— |
| 22 | —CH(CH$_3$)— | —CH(OH)— |
| 23 | —CH(CH$_3$)$_2$— | —CH(C$_6$H$_5$)* |
| 24 | —CH(CH$_2$)$_5$— | —CHCl— |

*C$_2$H$_5$ represents phenyl.

ANTI-TUMOR EVALUATION

The compounds used in this invention were evaluated against S180 ascites in female CFW Swiss mice. The mice were weighed (average weight: 20 g), placed into cages (six mice to a cage) and on day zero the mice were inoculated with 0.2 ml of a freshly prepared saline suspension (0.15M NaCl) containing $1 \times 10^7$ tumor cells/ml or a total of $2 \times 10^6$ cells. This inoculum was freshly prepared using "transfer" mice which had been injected with tumor cells the previous week; it was obtained via the following steps (1) the removal of cells from the peritoneal cavity of the sacrificed transfer mouse, (2) alternate centrifugation and washing operations (2-3 times with cold saline) to remove blood and other components, and (3) dilution of the volume of the packed cell with saline (1:3). A final centrifugation was carried out at 1000 RPM over a two minute period. A cell count was made on a 2000-fold dilution of this 1:3 suspension by means of a Coulter Counter. A final dilution to $1 \times 10^7$ cells/ml was made based on the average count.

On day 1, solutions of the test compounds were prepared and each mouse in a set of six was injected with the same test compound at the same dosage. The doses were based on the average weight of the animals (cage weight). Also, beginning on day 1 two controls were employed containing six mice per control:

(1) Normal Control: This consisted solely of the carrier or diluent used in combination with the test compound; and (2) Positive Control: This consisted solely of the known anti-tumor agent cis-[Pt(NH$_3$)$_2$Cl$_2$] in saline (8 mg/kg) to test the response of the biological system.

The effectiveness of a test compound was measured in terms of the % increase in life span (% ILS) of the test mice relative to the Normal Control (Calculated from the day of tumor inoculation, i.e., day zero). To standardize the test data and permit intercomparisons, the day of evaluation was arbitrarily taken as that day corresponding to twice the mean life span (or average day of death) of the control. This established a practical upper limit of 100% on the % ILS attainable. For calculation purposes the survivors on the day of evaluation were considered to have died on that day. The % ILS was calculated as follows:

% ILS = mean-life span of test mice/mean-life span of control mice $- 1 \times 100$ ILS values in excess of 50% were interpreted as being indicative of anti-tumor cell activity in animals whereas, values in excess of 75% indicated excellent activity.

The test compounds were evaluated in water. The results of these tests are shown in Table 3:

TABLE 3

| Example; (Compound) | Dose (mg/kg) | % ILS | Survivors | Positive Control % ILS | Positive Control Survivors |
|---|---|---|---|---|---|
| Ex. 1 K$_2$[Pd(Ethylmalonate)$_2$] | 5 | 6 | 0 of 6 | 41 | 0 of 6 |
| | 10 | −3 | 0 of 6 | | |
| | 20 | −7 | 0 of 6 | | |
| | 40 | 9 | 0 of 6 | | |
| | 80 | −6 | 0 of 6 | | |
| | 160 | 94 | 5 of 6 | | |
| | 320 | −13 | 0 of 6 | | |
| | 10 | −3 | 0 of 6 | 52 | 1 of 6 |
| | 20 | 4 | 0 of 6 | | |
| | 40 | −6 | 0 of 6 | | |
| | 80 | 16 | 0 of 6 | | |
| | 160 | 55 | 1 of 6 | | |
| | 320 | −31 | 1 of 6 | | |
| Ex. 2 K$_2$[Pd(Ketomalonate)$_2$] | 10 | 4 | 0 of 6 | 41 | 0 of 6 |
| | 20 | 4 | 0 of 6 | | |
| | 40 | 4 | 0 of 6 | | |
| | 80 | 13 | 1 of 6 | | |
| | 160 | 81 | 5 of 6 | | |
| | 320 | 17 | 0 of 6 | | |
| Ex. 3 K$_2$[Pd(Methylmalonate)$_2$] | 6.25 | 11 | 0 of 6 | 61 | 2 of 6 |
| | 12.5 | 2 | 0 of 6 | | |
| | 25 | −6 | 0 of 6 | | |
| | 50 | 2 | 0 of 6 | | |
| | 100 | 54 | 2 of 6 | | |
| | 200 | 54 | 0 of 6 | | |
| | 400 | −83 | 0 of 6 | | |
| Ex. 4 K$_2$[Pd(Tartronate)$_2$] | 12.5 | 1 | 0 of 6 | 61 | 2 of 6 |
| | 25 | 12 | 0 of 6 | | |
| | 50 | 11 | 0 of 6 | | |
| | 100 | 68 | 3 of 6 | | |
| | 200 | 76 | 0 of 6 | | |
| | 400 | 14 | 3 of 6 | | |
| Ex. 5 K$_2$[Pd(Phthalate)$_2$] | 50 | 18 | 0 of 6 | 91 | 4 of 6 |
| | 100 | 38 | 1 of 6 | | |
| | 200 | 79 | 2 of 6 | | |
| | 400 | 25 | 0 of 6 | | |
| Ex. 6 K$_2$[Pd(Cyclobutanedicarboxylate)$_2$] | 10 | −4 | 0 of 6 | 47 | 0 of 6 |
| | 20 | 9 | 0 of 6 | | |
| | 40 | 7 | 0 of 6 | | |
| | 80 | −7 | 0 of 6 | | |
| | 160 | 50 | 0 of 6 | | |
| | 320 | −75 | 0 of 6 | | |
| Ex. 7 K$_2$[Pd(Dimethylmalonate)$_2$] | 10 | −15 | 0 of 6 | 47 | 0 of 6 |
| | 20 | 0 | 0 of 6 | | |
| | 40 | −8 | 0 of 6 | | |
| | 80 | −11 | 0 of 6 | | |
| | 160 | 61 | 1 of 6 | | |
| | 320 | 26 | 0 of 6 | | |
| K$_2$[Pd(Malonate)$_2$] | 10 | 6 | 0 of 6 | 86 | 0 of 6 |
| | 20 | −1 | 0 of 6 | | |
| | 40 | 9 | 0 of 6 | | |
| | 80 | 69 | 3 of 6 | | |
| | 160 | 82 | 2 of 6 | | |
| | 320 | −74 | 0 of 6 | | |
| | 10 | 8 | 0 of 6 | 75 | 2 of 6 |
| | 20 | 8 | 0 of 6 | | |
| | 40 | −12 | 0 of 6 | | |
| | 80 | 66 | 2 of 6 | | |
| | 160 | 86 | 3 of 6 | | |
| | 320 | −74 | 0 of 6 | | |
| K$_2$[Pd(Oxalate)$_2$] | 12.5 | 2 | 0 of 6 | 91 | 4 of 6 |
| | 25 | 33 | 0 of 6 | | |
| | 50 | −7 | 0 of 6 | | |
| | 100 | −9 | 1 of 6 | | |
| | 200 | −71 | 0 of 6 | | |

On the basis of Table 3 it can be concluded that the bis(dicarboxylato)palladate(II) compounds are effective against malignant animal tumor cells sensitive thereto.

The effective dose (ED$_{90}$), lethal dose (LD$_{50}$) and therapeutic index (TI) were determined via the method of Miller and Taiter (Reported by R. A. Turner, "Screening Methods in Pharmacology", Academic Press, New York, pages 61-62 (1965)).

The results of this test are shown in Table 4. In this study Ed$_{90}$ represents the dose which causes a 50% increase in life span (ILS) in 90% of the test animals (mice) determined graphically. The LD$_{50}$ value represents the lethal dose to 50% of said animals (Therapeutic Index = LD$_{50}$/Ed$_{90}$).

TABLE 4

| Example (Compound) | Best % ILS (Dosage) | ED$_{90}$ | LD$_{50}$ | Therapeutic Index |
|---|---|---|---|---|
| Ex. 1 K$_2$[Pd(Ethyl-malonate)$_2$] | 94(160 mg/kg) | 150 | 320 | 2.1 |
| Ex. 2 K$_2$[Pd(Keto-malonate)$_2$] | 81(160 mg/kg) | 200 | 400 | 2.0 |
| Ex. 3 K$_2$[Pd(Methyl-malonate)$_2$] | 54(100 mg/kg) | 160 | 180 | 1.1 |
| Ex. 4 K$_2$[Pd(Tartron-ate)$_2$] | 76(200 mg/kg) | 190 | 400 | 2.1 |
| Ex. 5 K$_2$[Pd(Phthal-ate)$_2$] | 79(200 mg/kg) | 220 | 500 | 2.3 |
| Ex. 6 K$_2$[Pd(Cyclobu-tanedicar-boxylate)$_2$] | 50(160 mg/kg) | 210 | 230 | 1.1 |
| Ex. 7 K$_2$[Pd(Dimethyl-malonate)$_2$] | 61(160 mg/kg) | 210 | 280 | 1.3 |
| K$_2$[Pd(Malon-ate)$_2$] | 82(160 mg/kg) | 120 | 230 | 1.9 |
|  | 86(160 mg/kg) | 120 | 230 | 1.9 |

All compounds (I) exhibit favorable therapeutic indices.

The products described herein are merely illustrative of the invention and they are capable of wide variation and modification. Alterations to the product molecule are within the skill of the artisan to effect and, therefore, any derivatives of the herein-described compounds which prove useful in the treatment of malignant animal tumor cells sensitive thereto are considered as being within the scope of this invention.

What is claimed is:

1. A method of treating malignant tumor cells in animals sensitive to a palladium (II) compound of the formula:

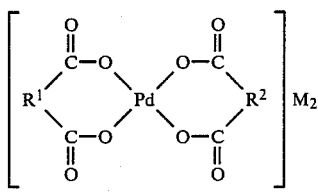

wherein R$^1$ and R$^2$ are the same or different and represent the following:

(a) methylene or ethylene;
(b) cycloalkylene of the formula:

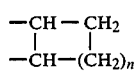

wherein n is an integer having a value of 2–3;
(c) alkylidene of 2–4 carbon atoms;
(d) cycloalkylidene containing 4–6 nuclear carbon atoms;
(e) o-phenylene of the formula:

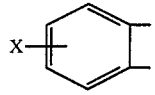

wherein X is selected from the group consisting of hydrogen, halogen and C$_{1-6}$ alkyl;
(f) aralkylidene of the formula:

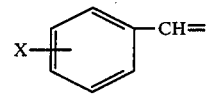

(g) substituted methylidene of the formula: =CR$^3$R$^4$ wherein R$^3$ and R$^4$ are selected from the group consisting of hydrogen, halogen and hydroxy; or
(h) keto; and M is an alkali metal or M$_2$ is an alkaline earth metal which comprises administering said compound to an animal afflicted with said tumor cells in an amount sufficient to cause regression of the same.

2. The method of claim 1 having the formula:

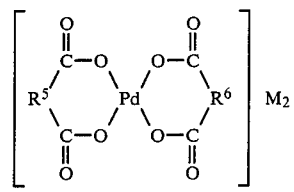

wherein R$^5$ and R$^6$ are identical moieties selected from among:
alkylidene of 2–4 carbon atoms;
cycloalkyidene containing from 4–6 nuclear carbon atoms;
o-phenylene of the formula:

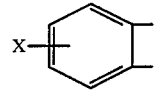

wherein X is selected from the group consisting of hydrogen, halogen and C$_{1-6}$ alkyl;
Hydroxymethylidene; and keto; and
M is an alkali metal.

3. The method of claim 2 wherein R$^5$ and R$^6$ are identical.

4. The method of claim 2 wherein R$^5$ and R$^6$ represent alkylidene of 2–4 carbon atoms.

5. The method of claim 4 wherein R$^5$ and R$^6$ represent ethylidene.

6. The method claim 2 wherein R$^5$ and R$^6$ represent o-phenylene.

7. The method of claim 2 wherein R$^5$ and R$^6$ represent hydroxymethylidene.

8. The method of claim 2 wherein R$^5$ and R$^6$ represent keto.

9. The method of claim 2 wherein R$^5$ and R$^6$ represents a cycloalkylidene containing 4–6 nuclear carbon atoms.

10. A composition for treating malignant animal tumor cells sensitive to a compound of the formula:

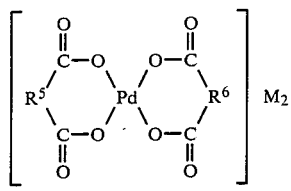

wherein $R^5$ and $R^6$ are identical moieties selected from among: alkylidene of 2-4 carbon atoms; cycloalkylidene containing from 4-6 nuclear carbon atoms o-phenylene of the formula:

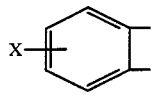

wherein X is selected from the group consisting of hydrogen, halogen, and $C_{1-6}$ alkyl;
hydroxymethylidene; and M is an alkali metal; in combination with a non-toxic pharmacologically acceptable inert carrier or diluent, said compound being present in an amount sufficient to cause regression of the tumor cells.

11. The composition of claim 10 wherein $R^5$ and $R^6$ are identical.

12. The composition of claim 10 wherein $R^5$ and $R^6$ represent alkylidene of 2-3 carbon atoms.

13. The composition of claim 12 wherein $R^5$ and $R^6$ represent ethylidene.

14. The composition of claim 10 wherein $R^5$ and $R^6$ represent o-phenylene.

15. The composition of claim 10 wherein $R^5$ and $R^6$ represent hydroxymethylidene.

16. The composition of claim 10 wherein $R^5$ and $R^6$ represent keto.

17. The composition of claim 10 wherein $R^5$ and $R^6$ represent a cycloalkylidene containing 4-6 nuclear carbon atoms.

18. The composition of claim 10 in a form suitable for parenteral administration.

19. The composition of claim 10 in a form suitable for oral administration.

20. The composition of claim 19 in the form of a tablet.

21. The composition of claim 19 in capsule form.

* * * * *